United States Patent [19]

Urano et al.

[11] Patent Number: 4,769,485
[45] Date of Patent: Sep. 6, 1988

[54] PREPARATION OF ALKENOYL ISOCYANATES

[75] Inventors: Satoshi Urano, Yawata; Noriyuki Tsuboniwa, Higashiosaka; Kei Aoki, Ikoma; Akira Matsumura, Hirakata; Yuji Suzuki, Suita; Ryuzo Mizuguchi, Yawata, all of Japan

[73] Assignee: Nippon Paint Co., Ltd., Osaka, Japan

[21] Appl. No.: 862,644

[22] Filed: May 13, 1986

[30] Foreign Application Priority Data

May 13, 1985 [JP] Japan .................. 60-101726
May 13, 1985 [JP] Japan .................. 60-101727
May 16, 1985 [JP] Japan .................. 60-105459
Apr. 8, 1986 [JP] Japan .................. 61-81544

[51] Int. Cl.$^4$ .................. C07D 118/04; C07D 263/08
[52] U.S. Cl. .................. 560/340; 548/226; 560/336; 560/338
[58] Field of Search .................. 260/453 A, 453 P; 548/226; 560/336, 338, 340

[56] References Cited

U.S. PATENT DOCUMENTS 3,155,700 11/1964 Steyermark .................. 260/545
3,709,895 1/1973 Kohlhaupt et al. .................. 548/226

FOREIGN PATENT DOCUMENTS 143613 6/1985 European Pat. Off. .
819100 7/1981 U.S.S.R. .................. 548/226

OTHER PUBLICATIONS

Gorbatenko et al., CA 84-30365z.
Speziale et al., CA 64-9577c.
Speziale et al., CA 64-5027c.
Speziale et al., CA 59-3903h.
Carelli et al., CA 56-10028i.
Kricheldorf et al., CA 98-107732r.
Urano et al., CA 103-124076u.
Lieser et al., Chem. Ber., 84, 4 (1951).
Diefenbach et al., Die Makromolekulare Chemie 131, 247 (1970).
Speziale et al., J. Org. Chem. 27, 3742 (1962).
Speziale et al., J. Org. Chem. 28, 1805 (1963).
Speziale et al., J. Org. Chem. 30, 4306 (1965).

Primary Examiner—Donald G. Daus
Assistant Examiner—Cecilia Shen
Attorney, Agent, or Firm—Wegner & Bretschneider

[57] ABSTRACT

A process for preparing alkenoyl isocyanates of the formula:

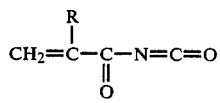

wherein R is a hydrogen atom or a lower alkyl group which comprises subjecting an oxazolinedione hydrohalide of the formula:

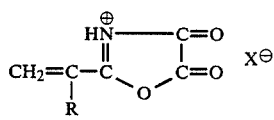

wherein X is a halogen atom and R is as defined above to decomposition under an ordinary pressure, in the presence of a hydrogen halide-eliminating agent and/or in a liquid medium having a dielectric constant of not more than 4.

8 Claims, No Drawings

PREPARATION OF ALKENOYL ISOCYANATES

The present invention relates to production of isocyanate compounds. More particularly, it relates to production of alkenoyl isocyanates of the formula:

$$\underset{R}{CH_2=C}-\underset{\underset{O}{\parallel}}{C}-N=C=O \quad (I)$$

wherein R is a hydrogen atom or a lower alkyl group (e.g. methyl, ethyl, propyl), particularly through oxazolinedione hydrohalides of the formula:

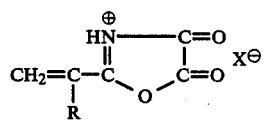

(III)

wherein X is a halogen atom (e.g. chlorine, bromine) and R is as defined above.

Throughout the specification, the term "lower alkyl" is intended to mean alkyl having 1 to 5 carbon atoms, preferably 1 to 3 carbon atoms, more preferably methyl. The term "halogen" is intended to mean chlorine, bromine, iodine and fluorine, inclusively. Among them, preferred are chlorine and bromine, particularly chlorine.

In general, compounds having an isocyanate group are widely used in the field of polymer chemistry because of their excellent reactivity. Particularly, those having a polymerizable double bond and an isocyanate group in the molecule are expected to have great usefulness, because the double bond and the isocyanate group can respectively participate in various reactions depending upon different reaction mechanisms. Specific examples are vinyl isocyanate (Angew. Chem., Int. Ed., 18, 319 (1979)), isocyanatoethyl methacrylate (Japanese Patent Publn. (unexamined) No. 5921/79), acryloyl isocyanate (Chem. Ber., 84, 4 (1951)), methacryloyl isocyanate (Chem. Ber., 84, 4 (1951)), etc.

Among them, the alkenoyl isocyanates (I) such as acryloyl isocyanate (I: R=hydrogen) and methacryloyl isocyanate (I: R=methyl) are particularly interesting in that the reactivities of the polymerizable double bond and the isocyanate group are enhanced by the carbonyl group present between them. The alkenoyl isocyanates (I) can thus undertake various reactions such as radical polymerization, anion polymerization, dimerization, trimerization, polar addition and addition of active hydrogen based on the partial structure (A) (i.e. conjugated double bond structure) and/or on the partial structure (B) (i.e. acylisocyanate structure) as set forth below and may be used as the industrial starting materials in various chemical fields:

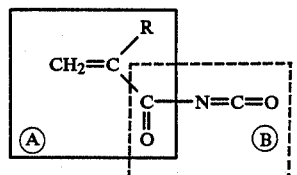

The alkenoyl isocyanates (I) were originally prepared by reacting the corresponding alkenoyl chlorides with silver isocyanate (Chem. Ber., 84, 4 (1951)). Apparently, this process is industrially disadvantageous in using an expensive reagent such as silver isocyanate. There is also known the process wherein isocyanic acid is used in place of silver isocyanate (U.S. Pat. No. 3,155,700). In this process, however, isocyanic acid is produced by heat decomposition of its trimer, i.e. isocyanuric acid, at such a high temperature as 620° C. In addition, isocyanic acid is a gaseous material. Accordingly, a special apparatus is needed, and handling of the gaseous material is troublesome.

In 1962 to 1965, Speziale et al developed a process for production of acyl isocyanates from amides by reacting the latter with oxalyl chloride (J. Org. Chem., 27, 3742 (1962); ibid., 23, 1805 (1963); ibid., 30, 4306 (1965)). By application of this process, Urano et al recently provided the industrial production of the alkenoyl isocyanates (I) from acrylamide or methacrylamide and an oxalyl halide (EP-A No. 0143613). While the process as provided by Urano et al affords the alkenoyl isocyanates (I) in relatively good yields, by-production of the corresponding haloalkanoyl isocyanates of the formula:

$$\underset{R}{XCH_2-CH}-\underset{\underset{O}{\parallel}}{C}-N=C=O \quad (II)$$

wherein R and X are each as defined above to a certain extent is unavoidable so that the application of a troublesome purification procedure to the reaction mixture is needed.

Diefenbach et al reported that the reaction of methacrylamide with oxalyl chloride at such a low temperature as −50° C. gives 2-isopropenyloxazoline-4,5-hydrochloride (III: R=CH₃; X=Cl) in a yield of 76% (Die Makromolekulare Chemie, 131, 247 (1970)). They also reported that when said 2-isopropenyloxazoline-4,5-dione hydrochloride is heated at 100° C. under a reduced pressure of 15 Torr, there is produced alpha-methyl-beta-chloropropionyl isocyanate (II: R=CH₃; X=Cl) (Die Makromolekulare Chemie, 131, 247 (1970)). According to them, this reaction was assumed to proceed through methacryloyl isocyanate (I: R=CH₃), but this intermediary product was not actually separated.

Aiming at improvement of the process of Urano et al as stated above, an extensive study has been carried out. As the result, it has now been found that production of the alkenoyl isocyanate (I) from acrylamide or methacrylamide and an oxalyl halide through the oxazolinedione hydrohalide (III) as once produced has various industrial advantages in comparison with the direct production of the alkenoyl isocyanate (I) from acrylamide or methacrylamide and an oxalyl halide. For instance, the alkenoyl isocyanate (I) is normally obtained in a liquid state and quite sensitive to moisture. To the contrary, the oxazolinedione hydrohalide (III) is usually obtained in a solid state and relatively stable to moisture. Thus, the oxazolinedione hydrohalide (III) is suitable for storage in industrial scale. Further, for instance, the oxazolinedione hydrohalide (III) can be readily separated from unfavorable impurities such as unreacted oxalyl halide so that the alkenoyl isocyanate (I) is obtainable in a higher purity with somewhat a higher yield. Besides, the oxazolinedione hydrohalide (III) is polymerizable so that it can be used as the monomeric component for production of polymeric materials.

According to the present invention, there is provided a process for preparing the alkenoyl isocyanate (I) which comprises subjecting the oxazolinedione hydrohalide (III) to decomposition under an ordinary pressure, in the presence of a hydrogen halide-eliminating agent and/or in a liquid medium having a dielectric constant of not more than 4, said oxazolinedione hydrohalide (III) being preferably produced by the reaction between an alkenylamide of the formula:

(IV)

wherein R is as defined above and an oxalyl halide of the formula:

(V)

wherein X is as defined above, the reaction being carried out by adding portionwise said alkenylamide to said oxalyl halide charged in a reactor.

In the process of this invention, the starting oxazolinedione hydrohalide (III) may be the one as produced by any process. Preferably, however, it is the one as produced by the reaction between the alkenylamide (IV) and the oxalyl halide (V), the reaction being carried out by adding portionwise the alkenylamide (IV) to the oxalyl halide (V) previously charged in a reactor.

As stated above, Diefenbach et al succeeded in production of 2-isopropenyloxazoline-4,5-dione hydrochloride (III: R=CH$_3$; X=Cl) from methacrylamide (IV: R=CH$_3$) and oxalyl chloride (V: X=Cl). In their process, methacrylamide is charged in a reactor first, and then oxalyl chloride is portionwise added thereto at −50° C., whereby the reaction proceeds to give said oxazolinedione hydrochloride. When the reaction is effected at room temperature, the oxazolinedione hydrochloride is not obtainable, and instead, alpha-methyl-beta-chloropropionyl isocyanate (II: R=CH$_3$; X=Cl) is produced. Thus, a low temperature as −50° C. is essential for successful production of the oxazolinedione hydrochloride, but such low temperature is disadvantageous from the industrial viewpoint. Further, when acrylamide (IV: R=H) is used as the starting material, the corresponding oxazolinedione hydrochloride (III: R=H; X=Cl) is not obtainable even at such a low temperature as −50° C., and beta-chloropropionyl isocyanate (II: R=H; X=Cl) is obtained. Quite surprisingly, the mere change of the charging order of the reagents into a reactor overcomes those defects in the process of Diefenbach et al. Thus, charging of the oxalyl halide (V) first into a reactor and subsequent adding of the alkenylamide (IV) thereto according to this invention makes it possible to carry out the reaction between the alkenylamide (IV) and the oxalyl halide (V) at room temperature to give the oxazolinedione hydrohalide (III) in such a better yield as as 85% or more. Said procedure according to this invention can also makes it possible to obtain the oxazolinedione hydrohalide (III) even when alkenylamide (IV: R=H) is used as the starting material.

In the process of the invention, the oxazolyl halide (V) is thus charged in a reactor first, and then the alkenylamide (IV) is portionwise added thereto continuously or intermittently. The molar ratio of the alkenylamide (IV) and the oxalyl halide (V) may be usually about 1:1–3, preferably about 1:1–1.5.

Any reaction medium is not necessarily required to use, but its use is normally preferred for uniform and smooth processing of the reaction. Examples of the reaction medium are inert solvents such as hydrocarbons (e.g. benzene, toluene, hexane), ethers (e.g. diethyl ether, dioxane, tetrahydrofuran), esters (e.g. methyl acetate, ethyl acetate), etc. Particularly preferred are halogenated hydrocarbons, of which specific examples are carbon tetrachloride, chloroform, dichloromethane, 1,1-dichloroethane, 1,2-dichloroethane, 1,6-dichlorohexane, 1,5-dichloropentane, 1,2-dichloropropane, 1,3-dichloropropane, 2,2-dichloropropane, 1,1,1-trichloroethane, 1,1,2-trichloroethane, 1,1,1,2-tetrachloroethane, 1,1,2,2-tetrachloroethane, 1,4-dichlorobutane, 2,3-dichlorobutane, 1-chlorobutane, 2-chlorobutane, chlorobenzene, chlorocyclohexane, ethylene tetrachloride, trichloroethylene, pentachloroethane, chloropropane, 1,2-dichloroethylene, o-, m- or p-dichlorobenzene, o-, m- or p-chlorotoluene, 1,2,4-trichlorobenzene, bromobenzene, bromoethane, 1- or 2-bromopropane, 1- or 2-bromobutane, 1- or 2-bromopentane, o-, m- or p-bromotoluene, bromocyclohexane, bromochloroethane, 1-bromohexane, etc. When these insert solvents are used, either one or both of the alkenylamide (IV) and the oxalyl halide (V) may be previously dissolved or suspended therein.

The reaction temperature may be ordinarily from −50° C. to the decomposition temperature of the oxazolinedione hydrohalide (III), preferably from about 0° to 40° C. From the industrial viewpoint, the temperature around room temperature or under ice cooling is favorable.

For separation of the oxazolinedione hydrohalide (III) from the reaction mixture, there may be adopted any per se conventional separation procedure such as filtration or distillation under reduced pressure. Addition of seed crystals of the oxazolinedione hydrohalide (III) to the reaction mixture may be sometimes favorable to accelerate the precipitation of the oxazolinedione hydrohalide (III). However, separation of the oxazolinedione hydrohalide (III) from the reaction mixture is not necessarily required, insofar as the presence of the oxazolinedione hydrohalide (III) in the reaction mixture is assured.

The oxazolinedione hydrohalide (III) is then subjected to decomposition under the condition affording the alkenoyl isocyanate (I) predominantly or suppressing by-production of the haloalkanoyl isocyanate (II). One typical example of such condition is to carry out the decomposition under an ordinary pressure (atmospheric or autogenic). As stated above, Diefenbach et al carried out the decomposition of the oxazolinedione hydrohalide (III) at about 100° C. under reduced pressure. Adoption of the reduced pressure seems to be quite reasonable, because the decomposition of the oxazolinedione hydrohalide (III) is considered to give first the alkenoyl isocyanate (I), which would be then reacted with hydrogen halide as by-produced to give the haloalkanoyl isocyanate (II), and the reduced pressure may be effective in elimination of the by-produced hydrogen halide from the reaction system. Contrary to this expectation, it has been revealed that the reduced pressure is not effective for suppression of the by-production of the haloalkanoyl isocyanate (II), and rather the ordinary pressure is effective in such suppression.

When the decomposition is effected under an ordinary pressure, the oxazolinedione hydrohalide (III) as charged in a reactor is heated until the decomposition proceeds sufficiently. Any reaction medium is not always required to use, but in the absence of any reaction medium, a higher temperature is normally needed. When, for instance, a reaction medium is used, the heat decomposition can take place at such a low temperature as about 40° C. In the absence of any reaction medium, heating up to the decomposition temperature of the oxazolinedione hydrohalide (e.g. about 102° to 103° C. in case of 2-isopropenyloxazoline-4,5-dione hydrochloride) is required. As the reaction medium, there may be used any inert solvent as hereinabove exemplified. The use of halogenated hydrocarbons as hereinabove exemplified is particularly preferred.

Another example of the condition is to carry out the decomposition in the presence of a hydrogen halide-eliminating agent. When the decomposition is effected in the presence of a hydrogen halide-eliminating agent under an ordinary or reduced pressure, there is predominantly produced the alkenoyl isocyanate (II).

As the hydrogen halide-eliminating agent, the use of such agent as not having an active hydrogen atom or as being reacted with a hydrogen halide not to produce an active hydrogen atom is favorable. Amines which are the most popular hydrogen halide-eliminating agents are hardly usable in the process of this invention. Specific examples of the preferred hydrogen halide eliminating agent are metal complex compounds (e.g. $(Ph_3P)_2Ru(CO)_3$, $(Ph_3)_3Pt$), metal halides (e.g. lithium chloride, titanium tetrachloride, aluminum chloride, cuprous chloride), synthetic zeolite (e.g. molecular sieve, microporous glass), etc. The hydrogen halide-eliminating agent is used normally in an amount of about 0.1 to 100 mol, preferably of about 0.1 to 10 mol.

The decomposition is usually effected by keeping the oxazolinedione hydrohalide (III) in the presence of the hydrogen halide-eliminating agent at a temperature of $-50°$ to 200° C., preferably from 0° to 150° C. under an ordinary or reduced pressure. A reduced pressure may afford sometimes a better result. Any reaction medium is not necessarily required to use. When used, any inert solvent as hereinabove exemplified may be employed.

Another example of the condition is to carry out the decomposition in the presence of a liquid medium having a dielectric constant of not more than 4. For such liquid medium, there may be used one or more of such inert solvents as aliphatic or alicyclic hydrocarbons (e.g. pentane, hexane, heptane, octane, decalin, cyclohexane), aromatic hydrocarbons (e.g. benzene, toluene, xylene, naphthalene), ethers (e.g. propyl ether, butyl ether, dioxane, isopropyl ether), esters and halogenated hydrocarbons (e.g. carbon tetrachloride). A dielectric constant of not more than 4 may be attained by the use of a single solvent or by the use of two or more solvents in combination.

The decomposition may be carried out by keeping the oxazolinedione hydrohalide (III) in a liquid medium of not more than 4 in dielectric constant at a temperature higher than the decomposition temperature of the oxazolinedione (III), usually from about 40° to 150° C., preferably from about 60° to 120° C., whereby the alkenoyl isocyanate (I) is predominantly produced.

Recovery of the alkenoyl isocyanate (I) from the reaction mixture may be accomplished by a per se conventional separation procedure such as filtration or distillation under atmospheric or reduced pressure.

In any of the above reactions and the post-treatments, a small amount of a polymerization inhibitor may be incorporated into the reaction system or the reaction mixture for prevention of the unnecessary polymerization on the double bond. Examples of the polymerization inhibitor are hydroquinone, p-methoxyphenol, 2,6-di-t-butyl-4-methylphenol, 4-t-butylcatechol, bisdihydroxybenzylbenzene, 2,2'-methylene-bis(6-t-butyl-3-methylphenol), 4,4'-butylidene-bis (6-t-butyl-3-methylphenol), 4,4'-thiobis(6-t-butyl-3-methylphenol), p-nitrosophenol, diisopropylxanthogenesulfide, N-nitrosophenylhydroxylamine ammonium salt, 1,1-diphenyl-2-picrylhydrazil, 1,3,5-triphenylpheldazyl, 2,6-di-t-butyl-alpha-(3,5-di-t-butyl-4-oxo-2,5-cyclohexadien-1-ylidene)-p-trioxy, 2,2,6,6-tetramethyl-4-piperidone-1-oxil, dithiobenzoyl sulfide, p,p'-ditolyl trisulfide, p,p'-ditolyl tetrasulfide, dibenzyl tetrasulfide, tetraethylthiuram disulfide, etc.

The alkenoyl isocyanates (I) are, in general, obtained in a liquid stable at room temperature and therefore can be handled with ease. They are soluble in various organic solvents and can be used in their solution form. When allowed to stand in the air, they are readily reacted with moisture in the air to give the corresponding amides. This property is meritorious from the viewpoint of environmental pollution. Their double bond is very reactive and can be readily reacted with other compounds to give isocyanate derivatives. Further, for instance, the alkenoyl isocyanates (I) exert a strong antimicrobial activity in their gaseous state and therefore are useful as antimicrobial agents. Furthermore, the alkenoyl isocyanates (I) can participate in various chemical reactions due to the functional groups present therein and therefore can be used for production of starting materials and intermediates in the fields of pharmaceuticals, agro-chemicals, dyestuffs, etc. Moreover, they have a wide use as monomers for production of various polymers. For instance, their copolymerization with styrene, alkyl acrylate, alkyl methacrylate or the like affords varnish resin. Further, for instance, their copolymerization with other monomers affords polymers useful as dyestuffs, adhesives, dipping agents, foaming agents, fiber treating agents, etc.

In general, the alkenoyl isocyanates (I) wherein R is lower alkyl are more stable than the one wherin R is hydrogen particularly when heated.

Practical and presently preferred embodiments of the invention are illustratively shown in the following Examples wherein part(s) and % are by weight unless otherwise indicated.

EXAMPLE 1

Preparation of 2-vinyloxazoline-4,5-dione hydrochloride (III: R=H; X=Cl)

Oxalyl chloride (130 g; 1.02 mol) was charged in a reactor, and a warm solution of acrylamide (71 g; 1.0 mol) in dichloroethane (250 ml) was dropwise added thereto (reaction temperature, 10° to 30° C.). After completion of the dropwise addition, the solvent and excess of the oxalyl chloride were removed by distillation under reduced pressure to obtain 2-vinyloxazoline-4,5-dione hydrochloride (161 g) as a yellow oil. Viscosity, 100,000 cp. Yield, 100%.

EXAMPLES 2 to 7

Preparation of 2-isopropenyloxazoline-4,5-dione hydrochloride (III: R=CH$_3$; X=Cl)

Oxalyl chloride was charged in a reactor, and methacrylamide or its organic solvent solution was dropwise added thereto in about 1 to 2 hours. After completion of the dropwise addition, 2-isopropenyloxazoline-4,5-dione hydrochloride was recovered from the reaction mixture by a per se conventional separation procedure. Decomposition point, 102° to 103° C.

In Example 2, a warm solution of methacrylamide in dichloroethane was dropwise added to oxaly chloride kept at room temperature (20° C.) while stirring. The resultant mixture was cooled with water to room temperature. The produced 2-isopropenyloxazoline-4,5-dione hydrochloride was collected by filtration under suction, washed with hexane and dried under reduced pressure.

In Example 3, a warm solution of methacrylamide in dichloroethane was dropwise added to oxalyl chloride under cooling with water while stirring. The produced 2-isopropenyloxazoline-4,5-dione hydrochloride was collected by filtration under suction and dried under reduced pressure.

In Example 4, methacrylamide was added portionwise to oxalyl chloride while stirring, whereby the reaction proceeded with generation of heat. At the stage that addition of 10 g of methacrylamide was completed, the reaction mixture was solidified. Dichloroethane (100 ml) was added thereto. The produced crystals were collected by filtration, washed and dried under reduced pressure to give 2-isopropenyloxazoline-4,5-dione hydrochloride.

Examples 5 to 7 were carried out in the same manner as in Example 2.

COMPARATIVE EXAMPLE 1

Preparation of 2-isopropenyloxazoline-4,5-dione hydrochloride (III: R=CH$_3$; X=Cl)

Methacrylamide was charged in a reactor, and while stirring, oxalyl chloride was dropwise added thereto in about 1 to 2 hours. With the progress of the dropwise addition, the reaction mixture changed to a brown, transparent resin. The resin was dissolved in dichloroethane (90 ml) and allowed to stand at room temperature, whereby 2-isopropenyloxazoline-4,5-dione hydrochloride was precipitated. The precipitate was collected by filtration and dried under reduced pressure. The reaction conditions and the yields in Examples 2 to 7 and Comparative Example 1 of the objective oxazolinedione hydrochloride are shown in Table 1.

TABLE 1

| Example No. | Methacrylamide (g/mol) | Oxalyl chloride (g/mol) | Molar ratio of acrylamide/oxalyl chloride | Solvent (ml) | Reaction temperature (°C.) | Yield (g/%) |
|---|---|---|---|---|---|---|
| 2 | 21.25/0.25 | 34.5/0.27 | 1/1.1 | Dichloroethane (90) | 55–68 | 37./86.2 |
| 3 | 106.2/1.25 | 174.0/1.375 | 1/1.1 | Dichloroethane (450) | 10–20 | 199.8/91.1 |
| 4 | 10.0/0.11 | 34.2/0.27 | 1/2.45 | — | 20–64 | 16.9/87.5 |
| 5 | 106.2/1.25 | 238/1.875 | 1/1.5 | Dichloroethane (450) | 10–20 | 198.7/90.6 |
| 6 | 106.2/1.25 | 158/1.25 | 1/1.0 | Dichloroethane (450) | 10–20 | 199.6/91.0 |
| 7 | 106.2/1.25 | 174.0/1.375 | 1/1.1 | Ethyl acetate (200) | 10–30 | 186.5/85.0 |
| Comparative 1 | 21.25/0.25 | 33.5/0.26 | 1/1.04 | — | 20–40 | 21.4/48.8 |

EXAMPLE 8

To 2-isopropenyloxazoline-4,5-dione hydrochloride (200 g; 1.14 mol), o-dichlorobenzene (800 g) was added, and the resultant mixture was heated to 140° C. while stirring for about 40 minutes. After cooling with water, the reaction mixture was distilled under reduced pressure to give methacryloyl isocyanate (70.9 g) and alpha-methyl-beta-chloropropionyl isocyanate (48.7 g).

EXAMPLE 9

To 2-isopropenyloxazoline-4,5-dione hydrochloride (200 g; 1.14 mol), dichloroethane (800 g) was added, and the resultant mixture was heated to 60°–65° C. while stirring for about 5.5 hours. After cooling with water, the reaction mixture was distilled under reduced pressure to give methacryloyl isocyanate (25.3 g) and alpha-methyl-beta-chloropropionyl isocyanate (80.7 g).

EXAMPLE 10

2-Isopropenyloxazoline-4,5-dione hydrochloride (100 g; 0.57 mol) was heated in nitrogen stream at 120° C. for about 20 minutes. After cooling with ice, the reaction mixture was distilled under reduced pressure to give methacryloyl isocyanate (30.2 g) and alpha-methyl-beta-chloropropionyl isocyanate (21.1 g).

EXAMPLE 11

To 2-vinyloxazoline-4,5-dione hydrochloride (100 g; 0.62 mol), o-dichlorobenzene (400 g) was added, and the resultant mixture was heated at 110° to 120° C. while stirring for about 30 minutes. After cooling with ice, the reaction mixture was distilled under reduced pressure to give acryloyl isocyanate (8.9 g) and beta-chloropropionyl isocyanate (56.4 g).

EXAMPLES 12 to 17

2-Isopropenyloxazoline-4,5-dione hydrochloride (8.775 g; 50 mmol) was dissolved in dichloroethane (44 ml), and molecular sieve was added thereto. The resultant mixture was heated at 80° C. for 1 hour while stirring. A portion of the reaction mixture was sampled, deuterated chloroform was added thereto, and NMR spectrum was measured. From the ratio of the absorption area of the methyl group ($\delta CH_3$: 1.87 ppm) in methacryloyl isocyanate to that of the methyl group ($\delta CH_3$: 1.32 ppm) in alpha-methyl-beta-chloropropionyl isocyanate, the molar ratio of methacryloyl isocyanate to alpha-methyl-beta-chloropropionyl isocyanate was determined. The results are shown in Table 2.

TABLE 2

| Example No. | Molecular sieve Kind | Amount (g) | Molar ratio of methacryloyl isocyanate/ α-methyl-β-chloro-propionyl isocyanate |
| --- | --- | --- | --- |
| 12 | 13 × 1/16 | 20 | 9.0 |
| 13 | 3A × 1/16 | 20 | 4.0 |
| 14 | 5A × 1/16 | 20 | 3.1 |
| 15 | AW-500 | 20 | 3.9 |
| 16 | 13 × 1/16 | 1 | 2.7 |
| 17 | 13 × 1/16 | 30 | 8.6 |

COMPARATIVE EXAMPLE 2

In the same manner as in Example 12 except that molecular sieve was not used, the operation was carried out. As the result, the molar ratio of methacryloyl isocyanate to alpha-methyl-beta-chloropropionyl isocyanate in the reaction mixture was 1.8:1.

EXAMPLE 18

In the same manner as in Example 12 except that cuprous chloride (4.950 g; 50 mmol) was used in place of molecular sieve, the operation was carried out. As the result, the molar ratio of methacryloyl isocyanate to alpha-methyl-beta-chloropropionyl isocyanate in the reaction mixture was 3.2:1.

EXAMPLE 19

Oxalyl chloride (139.6 g; 1.1 mol) and o-dichlorobenzene (400 g; dielectric constant, 9.88) were mixed together and cooled to a temperature of 0° to 10° C. Methacrylamide (85.1 g; 1.0 mol) was portionwise added thereto in 40 minutes, followed by stirring at 35° to 40° C. for 2 hours. A small amount of seed crystals of 2-isopropenyl-oxazoline-4,5-dione hydrochloride was added thereto, and the resultant mixture was allowed to stand whereby 2-iso-propenyloxazoline-4,5-dione hydrochloride was crystallized out.

To the above mixture comprising crystals of 2-iso-propenyloxazoline-4,5-dione hydrochloride, hexane (600 g; dielectric constant, 1.88) was added so that the dielectric constant of the solvent mixture was made to 3.45. Stirring was continued at a temperature of 70° to 75° C. for 1.5 hours. Distillation of the reaction mixture gave methacryloyl isocyanate (55.9 g). Yield, 88.4%.

EXAMPLES 20 to 24

In the same manner as in Example 19 except the reaction conditions were changed as shown in Table 3, the operation was carried out. The results are shown in Table 3.

TABLE 3

| Example No. | Methacrylamide (g) | Oxalyl chloride (g) | Molar ratio of methacrylamide/ oxalyl chloride | Products (% by weight) | | |
| --- | --- | --- | --- | --- | --- | --- |
| | | | | Methacryloyl isocyanate | α-Methyl-β-chloro-propionyl isocyanate | Residue |
| 20 | 48.4 | 75.8 | 1/1.05 | 84.8 | 6.6 | 4.5 |
| 21 | 48.4 | 75.8 | 1/1.05 | 87.3 | 2 | 3.7 |
| 22 | 85.1 | 128.2 | 1/1.01 | 58.3 | 5.7 | 13.2 |
| 23 | 85.1 | 139.6 | 1/1.1 | 88.0 | 0 | — |
| 24 | 85.1 | 139.6 | 1/1.1 | 83.0 | 1 | — |

EXAMPLE 25

Oxalyl chloride (139.6 g; 1.1 mol) and o-dichlorobenzene (400 g; dielectric constant, 9.88) were mixed together and cooled to a temperature of 0° to 10° C. Methacrylamide (85.1 g; 1.0 mol) was portionwise added thereto in 40 minutes. A small amount of seed crystals of 2-isopropenyloxazoline-4,5-dione hydrochloride was added thereto, and the resultant mixture was allowed to stand whereby 2-isopropenyloxazoline-4,5-dione hydrochloride was crystallized out. Hexane (600 g; dielectric constant, 1.88) was added thereto. Precipitated crystals were collected by filtration to obtain 2-isopropenyloxazoline-4,5-dione hydrochloride in a yield of 98.6%.

2-Isopropenyloxazoline-4,5-dione hydrochloride as obtained above (100 g) was suspended in a mixture of hexane (240 g) and o-dichlorobenzene (160 g), the dielectric constant of the solvent mixture being 3.45. The suspension was heated at a temperature of 70° to 75° C. under reflux for 1.5 hours. Distillation of the reaction mixture gave methacryloyl isocyanate (49 g; yield, 89.9%) and alpha-methyl-beta-chloropropionyl isocyanate (1.4 g; yield, 1.7%).

EXAMPLES 26 to 28

2-Isopropenyloxazoline-4,5-dione hydrochloride as obtained in Example 25 was subjected to decomposition under the conditions as shown in Table 4. The results are shown in Table 4.

TABLE 4

| Example No. | Solvent (molar ratio) | Dielectric constant | Products (% by weight) | | |
| --- | --- | --- | --- | --- | --- |
| | | | Methacryloyl isocyanate | α-Methyl-β-chloro-propionyl isocyanate | Residue |
| 26 | Hexane | 1.88 | 62 | — | 11.0 |
| 27 | o-Dichlorobenzene/hexane (1:1.5) | 3.45 | 88.2 | — | 3.0 |
| 28 | o-Dichlorobenzene/hexane (1:1.5) | 3.45 | 88.4 | — | 4.8 |

EXAMPLES 29 AND 30 AND COMPARATIVE EXAMPLES 3 AND 4

In the same manner as in Example 19 but using the the conditions as shown in Table 5, the operation was carried out. The results are shown in Table 5.

TABLE 5

| Example No. | Molar ratio of methacryl- amide/oxalyl chloride | Reaction temperature (°C.) | Solvent on decomposition (molar ratio) | Concentration (ml/mol) | Temperature for decomposition (°C.) | Dielectric constant | Yield of isocyanates (%) | Molar ratio of methacryloyl isocyanate/α-methyl chloropropionyl isocyanate |
|---|---|---|---|---|---|---|---|---|
| 30 | 1/1.05 | 0–10 | o-Dichloro-benzene/hexane (1:1.5) | 823 | 70–75 | 3.45 | 89.3 | 44:1 |
| 31 | 1/1.1 | 0–10 | o-Dichloro-benzene/hexane (1:1.5) | 823 | 70–75 | 3.45 | 88.0 | 90:1 |
| Comparative | | | | | | | | |
| 3 | 1/1.09 | 2–7 | Chloroform | 545 | 63 | 4.80 | 40.1 | 0.95:1 |
| 4 | 1/1.47 | −16~−19 | Dichloroethane | 504 | 70–83 | 10.44 | 84.3 | 1.5:1 |

What is claimed is:

1. A process for preparing alkenoyl isocyanates of the formula:

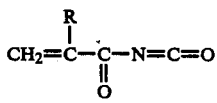

wherein R is a hydrogen atom or a lower alkyl group which comprises subjecting an oxazolinedione hydrohalide of the formula:

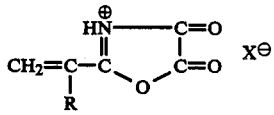

wherein X is a halogen atom and R is as defined above to decomposition under an ordinary pressure and in a liquid medium having a dielectric constant of not more than 4.

2. The process according to claim 1, wherein R is methyl and X is chlorine.

3. The process according to claim 1, wherein R is hydrogen and X is chloride.

4. The process for preparing alkenoyl isocyanates of the formula:

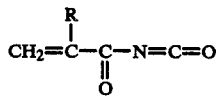

wherein R is a hydrogen atom or a lower alkyl group which comprises subjecting an oxazolinedione hydrohalide of the formula:

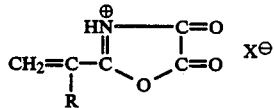

wherein X is a halogen atom and R is as defined above to decomposition, wherein the decomposition is effected under an ordinary pressure.

5. The process for preparing alkenoyl isocyanates of the formula:

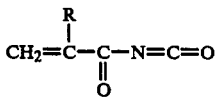

wherein R is a hydrogen atom or a lower alkyl group which comprises subjecting an oxazolinedione hydrohalide of the formula:

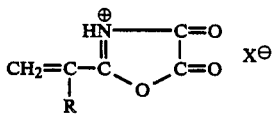

wherein X is a halogen atom and R is as defined above to decomposition, wherein the decomposition is effected in a liquid medium having a dielectric constant of not more than 4.

6. The process according to claim 1, wherein the oxazolinedione hydrohalide is the one produced by the reaction between an acrylamide of the formula:

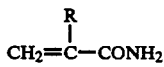

wherein R is as defined in claim 1 and an oxalyl halide of the formula:

wherein X is as defined in claim 1, the reaction being carried out by adding portionwise said acrylamide to said oxalyl halide charged in a reactor.

7. A process for preparing alkenoyl isocyanates of the formula:

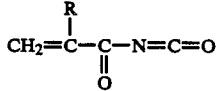

wherein R is a hydrogen atom or a lower alkyl group which comprises charging an oxalyl halide of the formula:

wherein X is a halogen atom and an inert solvent into a reactor, adding an acrylamide of the formula:

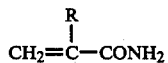

wherein R is as defined above portionwise thereto at a temperature of 0° to 25° C. to produce an oxazolinedione hydrohalide of the formula:

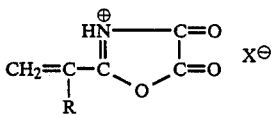

wherein R and X are each as defined above, adding seed crystals of the oxazolinedione hydrohalide to the reaction mixture comprising the produced oxazolinedione hydrohalide to crystallize out the oxazolidinedione hydrohalide and subjecting the oxazolinedione hydrohalide as crystallized out to decomposition in a liquid medium having a dielectric constant of not more than 4 at a temperature of 40° to 150° C. under an ordinary pressure.

8. The process according to claim 7, wherein the oxazolidinedione hydrohalide as crystallized out is once collected from the reaction mixture comprising the same prior to subjecting to decomposition.

* * * * *